(12) United States Patent
Schuck et al.

(10) Patent No.: US 8,738,383 B2
(45) Date of Patent: May 27, 2014

(54) REMOTELY AND INTERACTIVELY CONTROLLING SEMI-AUTOMATIC DEVICES

(75) Inventors: Joseph C. Schuck, McMurray, PA (US); Philip H. Spano, Jr., McKees Rocks, PA (US)

(73) Assignee: Aesynt Incorporated

( * ) Notice: Subject to any disclaimer, the term of this patent is extended or adjusted under 35 U.S.C. 154(b) by 1360 days.

(21) Appl. No.: 11/759,438

(22) Filed: Jun. 7, 2007

(65) Prior Publication Data

US 2008/0306740 A1 Dec. 11, 2008

(51) Int. Cl.
*G10L 15/00* (2013.01)

(52) U.S. Cl.
USPC .......................... 704/275; 700/231

(58) Field of Classification Search
USPC ................................ 704/270–278
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,389,917 A | 2/1995 | LaManna et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |

(Continued)

*Primary Examiner* — Douglas Godbold
*Assistant Examiner* — Mark Villena
(74) *Attorney, Agent, or Firm* — Alston & Bird LLP (57) ABSTRACT

An apparatus, system, method and computer program product are provided for enabling a user to remotely and interactively control, using voice commands, the processing tasks of multiple pieces of equipment, such as semi-automatic medication storing, dispensing and packaging devices. In particular, an apparatus may be configured to provide a user with a voice prompt associated with a dynamically prioritized task. In response, the apparatus may further be configured to receive, a voice command from the use and to transmit an instruction associated with the voice command to one of the multiple pieces of equipment for performance of the prioritized task.

31 Claims, 6 Drawing Sheets

(56) References Cited

U.S. PATENT DOCUMENTS

| | | |
|---|---|---|
| 5,971,594 A | 10/1999 | Sahai et al. |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,119,179 A | 9/2000 | Whitridge et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,289,656 B1 | 9/2001 | Wangu et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,609,047 B1 | 8/2003 | Lipps |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,732,884 B2 | 5/2004 | Topliffe et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,804,654 B2 | 10/2004 | Kobylevsky et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,058,584 B2 | 6/2006 | Kosinski et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| 7,408,439 B2 * | 8/2008 | Wang et al. ............ 340/3.7 |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 2003/0149599 A1 * | 8/2003 | Goodall et al. ............ 705/2 |
| 2003/0220815 A1 * | 11/2003 | Chang et al. ............ 705/2 |
| 2004/0054207 A1 * | 3/2004 | Katragadda et al. ........ 718/102 |
| 2004/0059582 A1 * | 3/2004 | Kumhyr ................ 704/275 |
| 2004/0133705 A1 * | 7/2004 | Broussard et al. ........ 710/1 |
| 2004/0158507 A1 * | 8/2004 | Meek et al. ............ 705/28 |
| 2005/0098626 A1 * | 5/2005 | Jordan et al. ........... 235/381 |
| 2005/0113969 A1 * | 5/2005 | Spano et al. ........... 700/237 |
| 2005/0184151 A1 * | 8/2005 | DiMaggio et al. ........ 235/385 |
| 2005/0187791 A1 * | 8/2005 | DiMaggio et al. ........ 705/2 |
| 2005/0202843 A1 * | 9/2005 | Fors et al. ........... 455/556.1 |
| 2005/0222873 A1 * | 10/2005 | Nephin et al. .......... 705/2 |
| 2005/0251418 A1 * | 11/2005 | Fox et al. ............ 705/2 |
| 2006/0273168 A1 * | 12/2006 | Jordan et al. .......... 235/385 |
| 2007/0005413 A1 * | 1/2007 | Hennings et al. ........ 705/9 |
| 2007/0119930 A1 * | 5/2007 | Jordan et al. .......... 235/385 |
| 2007/0194939 A1 * | 8/2007 | Alvarez et al. ......... 340/573.1 |
| 2007/0233494 A1 * | 10/2007 | Shen et al. ........... 704/260 |

\* cited by examiner

REMOTELY AND INTERACTIVELY CONTROLLING SEMI-AUTOMATIC DEVICES

FIELD OF THE INVENTION

In general, exemplary embodiments of the present invention relate to remote access and control of one or more pieces of equipment and, in particular, to the use of voice recognition to interactively manage the performance of a dynamically-prioritized plurality of tasks by the pieces of equipment.

BACKGROUND OF THE INVENTION

In many industries, workers are tasked with operating multiple pieces of equipment (e.g., electromechanical machines or robotics) at any given time in order to complete multiple different tasks or projects. While primarily automated, these pieces of equipment or devices often require at least some human intervention in order to complete a given task or project. For example, a user may need to interface with the semi-automatic device in order to instruct the device to begin the task or project, to intervene where, for example, consumable supplies associated with the device need replenished and/or a fault condition requiring attention has occurred, and/or simply to perform some portion of the task or project that the device cannot handle on its own. One such industry may, for example, be the pharmaceutical dispensing industry, wherein pharmacy technicians use semi-automated medication storing, dispensing and packaging devices, located within a hospital or an external pharmacy, to fill daily, weekly, monthly and/or one-time prescriptions for multiple patients.

While some of the tasks may require that the user physically interface with the device, many do not. However, current systems typically require that the user physically "visit" a piece of equipment in order to provide any instruction to the device and/or perform any task in relation to the device (e.g., to know if work is waiting to be performed, consumable supplies need replenished, and/or if a fault condition requiring attention has occurred). A consequence of this requirement is that a significant amount of unnecessary time and motion is expended in performance of tasks or projects in relation to the semi-automatic devices; thus resulting in built-in inefficiencies associated with completion of the tasks.

In addition to the foregoing, as noted above, a user may be tasked with completing multiple different tasks or projects within a given time period. In many cases certain tasks or actions arising in relation to these projects require more immediate attention than other such tasks or actions. In addition, it may be beneficial to give certain projects, or tasks within that project, priority over other tasks or projects in order to more efficiently complete all of the projects for which the user is responsible. It may be very difficult for users to process all of the factors that go into determining which task or action should be performed at what time and in what order in order to ensure that all projects are completed in a timely fashion.

A need, therefore, exists not only for a way in which users can remotely interact with and control the processing tasks of multiple pieces of equipment, but also for a way in which tasks and/or projects associated with the pieces of equipment can be prioritized and automatically provided to the user, such that the user need not keep track of every task to be performed and its relation to other tasks to be performed.

BRIEF SUMMARY OF THE INVENTION

In general, exemplary embodiments of the present invention provide an improvement over the known prior art by, among other things, providing a mobile device or apparatus that enables a user to remotely and interactively control the processing tasks of multiple pieces of equipment, such as electromechanical machines or robotics. Exemplary embodiments of the present invention further provide a method for dynamically prioritizing the processing tasks, and automatically pushing instructions relating to these processing tasks based on the dynamic prioritization.

In accordance with one aspect of the present invention, an apparatus is provided for remotely and interactively controlling one or more semi-automatic devices. In one embodiment, the apparatus may include an input device configured to receive information associated with two or more tasks to be performed in relation to the semi-automatic devices, an output device configured to communicate an instruction associated with at least one of the two or more tasks, and a processor in communication with the input and output devices. The apparatus of this embodiment may further include a memory in communication with the processor that stores information associated with the two or more tasks, as well as an application executable by the processor. The application may be configured, upon execution, to dynamically prioritize the two or more tasks based at least in part on a set of rules defining the relative priorities associated with the two or more tasks, and to automatically communicate, via the output device, an instruction associated with one of the two or more tasks based at least in part on the dynamic prioritization.

According to another aspect of the present invention, a system is provided. In one exemplary embodiment, the system may include one or more semi-automatic devices and an apparatus configured to receive and store information associated with two or more tasks to be performed in relation to the one or more semi-automatic devices. The apparatus of this exemplary embodiment may further be configured to dynamically prioritize the two or more tasks based at least in part on a set of rules defining the relative priorities associated with the two or more tasks, and to communicate an instruction associated with one of the two or more tasks based at least in part on the dynamic prioritization.

In accordance with yet another aspect of the present invention, a method is provided. In one exemplary embodiment, the method may include: (1) receiving information associated with two or more tasks to be performed in relation to one or more semi-automatic devices; (2) dynamically prioritizing the two or more tasks based at least in part on a set of rules defining the relative priorities associated with the two or more tasks; and (3) communicating an instruction associated with one of the two or more tasks based at least in part on the dynamic prioritization.

According to another aspect of the present invention, an apparatus is provided. The apparatus of one exemplary embodiment may include an input device configured to receive an instruction associated with a task to be performed by one of a set of semi-automated devices, said instruction based on a dynamic prioritization of a plurality of tasks to be performed by the set of semi-automated devices, an output device configured to output an audible prompt associated with the instruction, and a processor in communication with the input and output devices. The apparatus may further include a memory in communication with the processor and storing an application executable by the processor. In one exemplary embodiment, the application may be configured, upon execution, to convert the instruction into the audible prompt.

In accordance with yet another aspect of the invention, a computer program product is provided for remotely and interactively controlling one or more semi-automatic devices. The computer program product contains at least one computer-readable storage medium having computer-readable program code portions stored therein. The computer-readable program code portions of one exemplary embodiment include: (1) a first executable portion for receiving information associated with two or more tasks to be performed in relation to one or more semi-automatic devices; (2) a second executable portion for dynamically prioritizing the two or more tasks based at least in part on a set of rules defining the relative priorities associated with the two or more tasks; and (3) a third executable portion for communicating an instruction associated with one of the two or more tasks based at least in part on the dynamic prioritization

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Overview:

Exemplary embodiments of the present invention provide a mobile device or apparatus that enables a pharmacy technician, or other user, to remotely and interactively control the processing tasks of multiple pieces of equipment, such as semi-automatic medication storing, dispensing and packaging devices, or other electromechanical machines or robotics, using voice commands. The apparatus of one exemplary embodiment provides the user with voice instructions or prompts for performing certain actions or tasks with respect to the various medication storing and dispensing devices. The apparatus then converts the user's voice commands, which are received in response to the prompts or instructions, into data signals that can be wirelessly transmitted to the applicable medication storing, dispensing and packaging device for performing a particular task.

According to one exemplary embodiment, a central pharmacy server or main operating unit may maintain and dynamically prioritize a list of tasks to be performed in relation to the various medication storing and dispensing devices. The tasks may be prioritized based on a configurable set of rules defining the relative priority of each piece of equipment and the various tasks that are queued for performance in relation to that piece of equipment. The central pharmacy server may push instructions relating to the tasks, in an order corresponding to the prioritization, to the apparatus, causing the apparatus to then output to the pharmacy technician corresponding voice prompts or instructions for performing the pushed task. In one exemplary embodiment, the central pharmacy server may further prioritize the list of options provided to the user in voice prompts for performing the task. The prioritization may be based, for example, on the probability of the user selecting the option, as determined by historical data representing options previously selected by the user, or other users, in relation to respective tasks. The order in which the options are provided to the user may then be based on the relative priorities.

As another aspect of exemplary embodiments of the invention, multiple users may be able to remotely and interactively control the processing tasks of a single (or multiple) pieces of equipment at the same time via their respective mobile devices. The users may be prompted, such as via a designated channel (e.g., on a frequency associated with that user) or via a message addressed to the user's mobile device, by the central pharmacy server according to a configurable set of rules defining the priority of the user's work on the various pieces of equipment. This exemplary embodiment enables parallel tasks and work to be performed simultaneously and, where beneficial, for multiple users to more quickly complete the overall work at a single piece of equipment.

Exemplary embodiments of the present invention improve the efficiency of pharmacy operations, or operations in other industries, by affording technicians the ability to complete tasks, such as medication picking and restocking activities without the need to return to a computer workstation associated with the various pieces of equipment, thus significantly reducing the amount of time and motion associated with interfacing with the equipment. In addition, using the apparatus of exemplary embodiments, users are able to multitask, thus requiring less operators to be working to accomplish the same amount of work.

Figure 1:
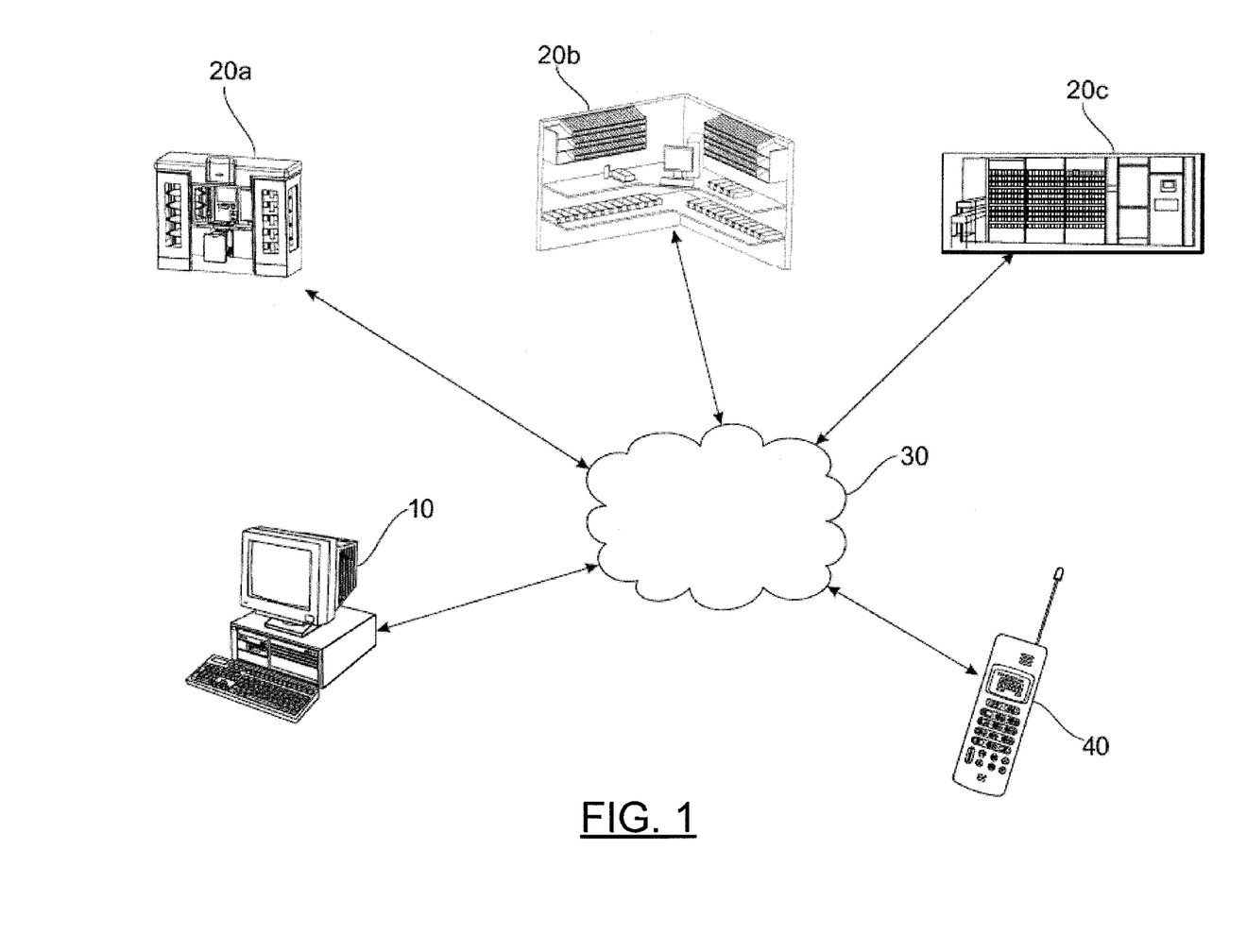
FIG. 1 is a block diagram of one type of system that would benefit from exemplary embodiments of the present invention.

Overall System:

Reference is now made to FIG. 1, which is a block diagram of an overall system that would benefit from exemplary embodiments of the present invention. As shown, the system may include a server or main operating unit 10 capable of accessing one or more semi-automatic devices 20A, 20B, 20C over a communication network 30 such as a Local Area Network (LAN), Wide Area Network (WAN), Wireless Local Area Network (WLAN), Wireless Wide Area Network (WWAN), or the like. The system of exemplary embodiments may further include a mobile device or apparatus 40 also able to communicate with the semi-automatic devices 20A, 20B, 20C, as well as the server 10 over the same or different communication network 30. While reference is made to a "server," one of ordinary skill in the art will recognize that exemplary embodiments of the present invention are not limited to use in a client-server environment, but may similarly be deployed in other computer architectures wherein electronic devices are capable of communicating back and forth with each other.

In one exemplary embodiment, the server 10 may be associated with a central pharmacy, and/or the semi-automatic devices 20A, 20B, 20C may include one or more medication storing, dispensing and packaging devices such as the Med- Carousel®, Medshelf®, ROBOT-Rx® and/or Intellishelf-Rx™ offered by McKesson Corporation. As one of ordinary skill in the art will recognize, however, exemplary embodiments of the invention are not limited to use in relation to the pharmaceutical industry and medication storing, dispensing and packaging devices. In contrast, the system of exemplary embodiments may include any semi-automatic device or piece of equipment in relation to which one or more tasks or actions may be performed.

Figure 2:
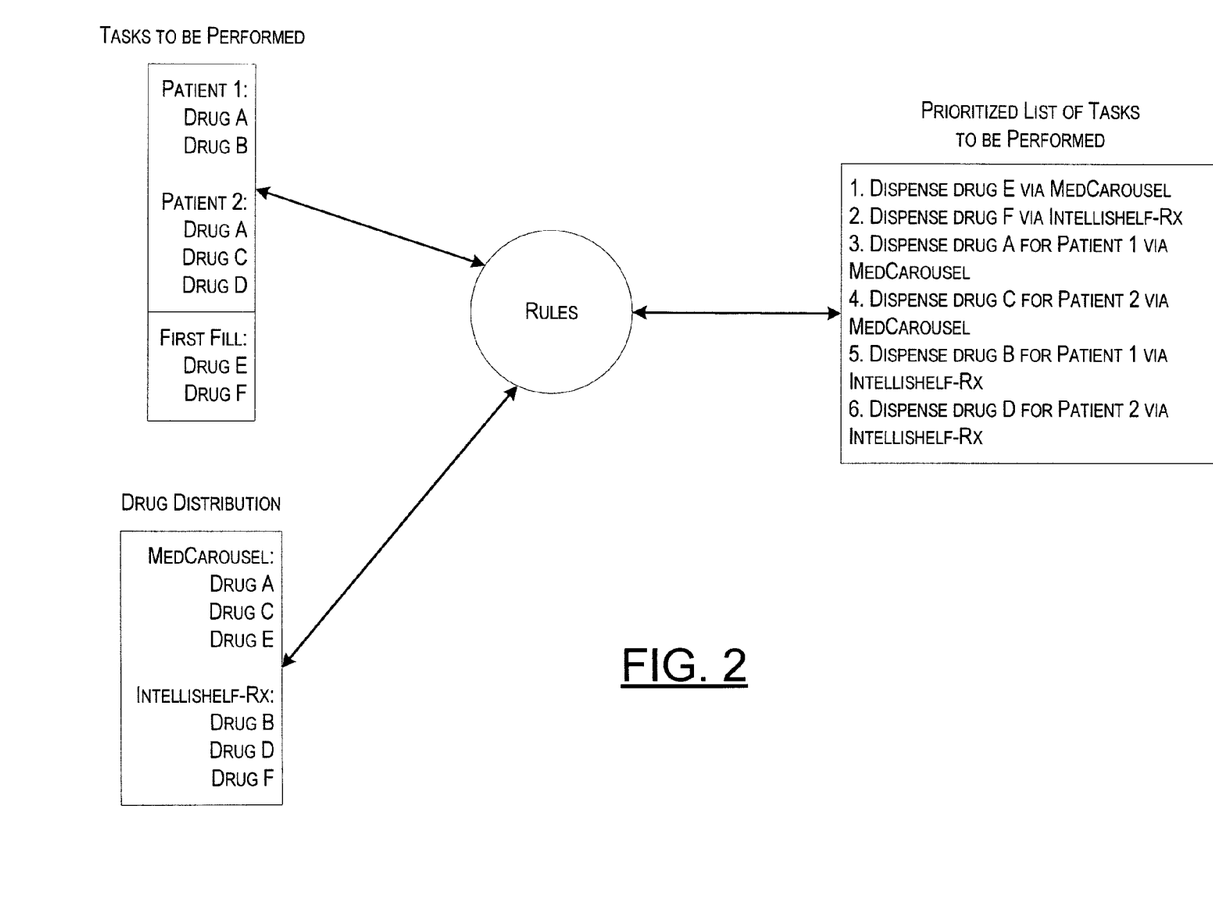
FIG. 2 illustrates how a set of tasks may be prioritized in accordance with one exemplary embodiment of the present invention.

In one exemplary embodiment, the server 10, which is shown in more detail in FIG. 2, may be responsible for receiving and storing one or more tasks or actions to be performed in relation to the semi-automatic devices 20A, 20B, 20C. These tasks may include, for example, a list of patient's whose daily medications need dispensing, a list of first dose medications needed for one or more new patients, an instruction to generate one or more reports, a list of one or more medications that need to be packaged, labeled and/or restocked, an instruction to go witness the restocking of a medication in a particular device, and the like. The server 10 may periodically receive these tasks from various sources. For example, a user may input information relating to a particular task directly into the server 10 via an input device, such as a keypad or touch screen. Alternatively, or in addition, one or more tasks may be received via a communication network 30 from a remote location, such as a nurse's workstation (e.g., as he or she is inputting a patient's prescription needs). As another example, tasks may be received via other programs or code modules within the overall system, such as where a program periodically wakes up, checks the status of certain machines and/or tasks, and generates a resulting one or more tasks. In addition, one or more tasks may be generated by the electronic devices themselves, such as when, for example, a machine runs out of a consumable or stocks out of a medication stored by the device, a machine error occurs, or the like.

In some instances, in addition to receiving information associated with one or more tasks from various sources, the server 10 may be required to request and obtain additional information regarding the received tasks. For example, where the task is to fill a first dose of a specific medication, the server 10 may need to determine in which medication storing, dispensing and packaging device the specified medication is located. This may be done, for example, by accessing a database including a description of the medications stored in each of the medication storing, dispensing and packaging devices. Where, for example, more than one device stores a particular medication, it may be the user's preference as to which of the devices storing the medication is used to fulfill the particular task at hand. In this exemplary embodiment, the server 10 may need to obtain additional information that can be used to generate and provide a recommendation as to which device to use. The information may include, for example, on the expiration dates of the medications stored in the different devices, the amount of time the medication has been sitting in the respective devices, and the like.

Upon receiving and storing the one or more tasks to be performed in relation to the various semi-automatic devices 20A, 20B, 20C, the server 10 of one exemplary embodiment may dynamically prioritize the list of tasks to be performed. In particular, according to one exemplary embodiment, the server 10 may store a set of rules defining the relative priorities of one or more tasks, or types of tasks, to be performed and/or one or more semi-automatic devices associated with the tasks. For example, one rule may state that all requests to dispense a first dose medication from any of the medication storing, dispensing and packaging devices take priority over any other requests. Alternatively, or in addition, one rule may state that all incoming tasks to be performed in relation to the MedCarousel® medication storage and retrieval system take precedence over tasks to be performed in relation to the Intellishelf-Rx™ medication storage and dispensing device. The rules may periodically change depending upon the time of day, the amount of work currently being performed in relation to a particular device, the number of tasks in the queue in relation to a particular device, the location of the pharmacy technician, or other user, in relation to the various devices, the amount of time a particular task has been sitting in the queue (e.g., a rule may specify that any task remaining in the queue for more than two hours is automatically placed at the top of the queue), the inventory conditions of the various devices (e.g., if and when a particular medication stocks out), or the like. In one exemplary embodiment, the rules may change based on the "availability" of a particular device, as determined, for example, by the task currently being performed by the device. By way of example, assume that a pharmacy's most critical operation is a cart or batch cabinet fill, which is highly repetitive. While a device is completing this particular task, that device may be deemed less "available" than other devices performing other tasks, since it is desirable to limit the number of interruptions to a cabinet fill because of the affect of interruptions on the device's efficiency. Using the set of rules, the server 10 may, for example, prioritize the tasks to be performed each time a new task is received and/or after some predetermined amount of time (e.g., every 10 minutes) has lapsed. FIG. 2 provides an exemplary illustration of how a set of tasks to be performed may be prioritized based on the above exemplary rules.

In one exemplary embodiment, in addition to prioritizing the tasks in the manner described above, the server 10 may be further configured to prioritize the list of choices or actions to be taken in response to, or in order to fulfill, the task. To illustrate, where for example the task is to respond to a printer associated with a particular device running out of ribbon, the actions that may be taken in response to the task, and which may be provided as options or choices to the user, may include, for example, to do nothing, switch to a new printer, or change the mode of operation (i.e., move to a new task) until someone can change the printer ribbon. According to one exemplary embodiment, the server 10 may prioritize these actions or choices based on the probability that the user with select each option or take each action and then present the actions or choices in order of priority. In one exemplary embodiment, the probability that a user will select each option may be based on historical data representing options previously selected by the user, or other users, in relation to the corresponding task. In this manner, the prioritization of the actions or options may be performed dynamically as additional historical data is collected.

Based on the prioritized list of tasks and actions, the server 10 may then automatically push instructions for completing a task on the list to the mobile device 40 via the communication network 30. In one exemplary embodiment, the server 10 may wait until notice is received that a current task has been completed prior to pushing the instruction to the mobile device 40. Alternatively, where it is determined that a particular task requires immediate attention, the server 10 may immediately push the instruction to the mobile device 40, regardless of where the user is in the process of completing the current task. In one exemplary embodiment, the mobile device 40, which is discussed in more detail below in relation to FIG. 3, may receive the instruction, convert the instruction into a voice prompt, and output the voice prompt to the user operating the mobile device 40. In one exemplary embodiment, the mobile device 40 may also display the instruction via a display screen in addition to the voice prompt. In addition, the mobile device 40 may, in response to the voice prompt, receive a voice command and, in some instances, additional input data (e.g., information scanned from a selected medication) from the user, which the mobile device 40 may translate into an instruction for communicating to an appropriate one of the semi-automatic devices 20A, 20B, 20C for completion of the task. In this manner, a user is able to remotely control multiple semi-automatic devices based on a dynamic, prioritized list of tasks to be performed.

In another exemplary embodiment, the mobile device 40, and not the server 10, may receive, store and dynamically prioritize the list of tasks to be performed in relation to the semi-automatic devices 20A, 20B, 20C, as well as the actions or options for performing respective tasks. In this exemplary embodiment, a user may, for example, upload an original list of tasks to be performed from the server 10 to the mobile device 40 at the beginning of a work day or shift. The mobile device 40, and more specifically an application operating on the mobile device 40, may prioritize the original list based on the set of rules defining the relative priorities, as well as the actions associated with respective tasks based on the probabilities of selection. Thereafter, the mobile device 40 may periodically receive one or more additional tasks to be performed directly from the various sources discussed above (e.g., via an input device, via the communication network from a remote device, such as a nurse's workstation and/or from the devices themselves). The mobile device 10 may dynamically prioritize the list of tasks (e.g., after each new task is received and/or after some predetermined amount of time has lapsed), and output voice prompts to the user operating the mobile device 40 as instructions associated with each task based on its relative priority.

While not shown in FIG. 1, in yet another exemplary embodiment, the system may further include additional mobile devices, each operated by a different user in relation to the semi-automatic devices. Like the mobile device 40 discussed above, each of these additional mobile devices may be capable of receiving instructions for performing one or more tasks in relation to each of the semi-automatic devices, outputting voice prompts to the mobile device operator in relation to the instruction, receiving audible commands (and, in some instances, additional input data) in response to the prompts, and transmitting instructions to the corresponding semi-automatic devices based on the audible commands received. In this exemplary embodiment, prior to pushing instructions for performing a task in relation to one of the semi-automatic devices, the server 10 may first determine to which of the mobile devices to push the instruction. The determination may be made, for example, based on a current task being performed by each of the operators of the mobile devices, the location of the operators in relation to the various semi-automatic devices, to which semi-automatic devices respective users or mobile devices have subscribed, and/or other similar factors. The location of the operators may be determined in any number of ways including, for example, through the use of a Global Positioning System, or similar location, device, or based on the location of the device in relation to which the user most recently worked, just to name a few. In another exemplary embodiment, a separate list of tasks may exist for each mobile device, providing a dynamically prioritized list of tasks to be performed by the user operating that mobile device. In this exemplary embodiment, the server 10 may store each separate list, or, alternatively, each mobile device may store its own list of tasks and dynamically prioritize the list based on incoming tasks to be performed.

Server/Main Operating Unit and Mobile Device

Figure 3:
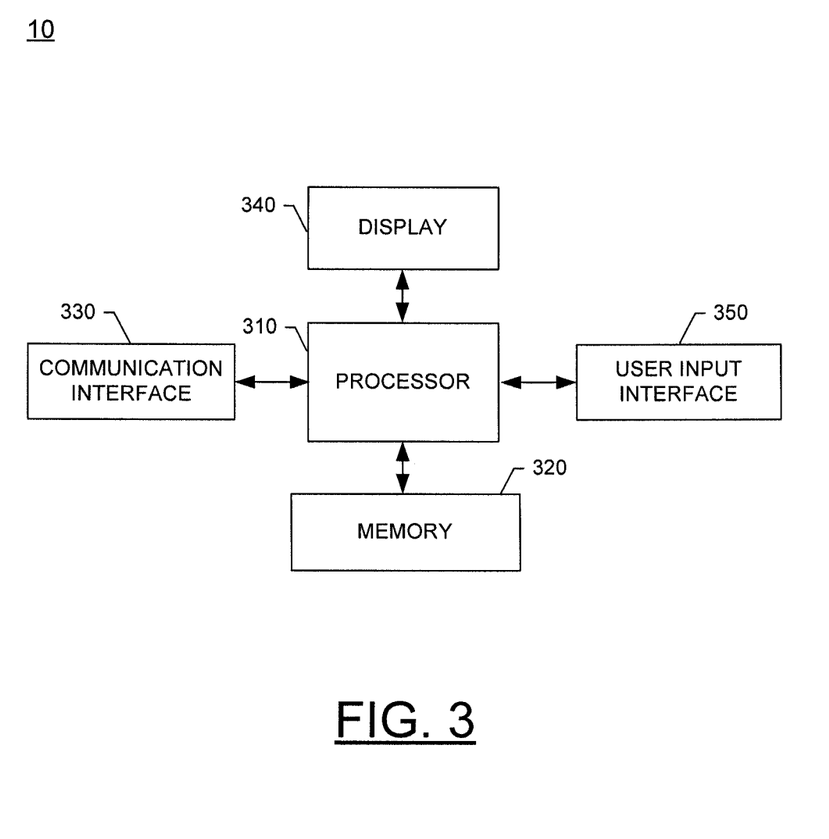
FIG. 3 is a schematic block diagram of an entity capable of operating as a pharmacy server or main operating unit in accordance with exemplary embodiments of the present invention.

Referring now to FIG. 3, a block diagram of an entity capable of operating as a server or main operating unit 10 is shown in accordance with one embodiment of the present invention. The entity capable of operating as a server 10 includes various means for performing one or more functions in accordance with exemplary embodiments of the present invention, including those more particularly shown and described herein. It should be understood, however, that one or more of the entities may include alternative means for performing one or more like functions, without departing from the spirit and scope of the present invention. As shown, the entity capable of operating as a server 10 can generally include means, such as a processor 310 connected to a memory 320, for performing or controlling the various functions of the entity. The memory can comprise volatile and/or non-volatile memory, and typically stores content, data or the like. For example, the memory typically stores content transmitted from, and/or received by, the entity. Also for example, the memory typically stores software applications, instructions or the like for the processor to perform steps associated with operation of the entity in accordance with embodiments of the present invention. As described above, the memory 320 may store one or more tasks to be performed in relation to one or more semi-automatic devices in communication with the server 10. The memory 320 may further store a set of rules defining the relative priorities of these tasks, as well as an application for dynamically prioritizing the list of tasks based at least in part on the set of rules. The memory 320 may further store historical data associated with actions taken or options selected for performing various tasks, as well as an application for dynamically prioritizing the list of actions or options associated with respective tasks based on the historical data.

In addition to the memory 320, the processor 310 can also be connected to at least one interface or other means for displaying, transmitting and/or receiving data, content or the like. In this regard, the interface(s) can include at least one communication interface 330 or other means for transmitting and/or receiving data, content or the like (e.g., for receiving the one or more tasks and for transmitting instructions for performing the tasks to the mobile device), as well as at least one user interface that can include a display 340 and/or a user input interface 350. The user input interface, in turn, can comprise any of a number of devices allowing the entity to receive data from a user, such as a keypad, a touch display, a joystick or other input device. As discussed above, in one exemplary embodiment, the user interface 350, such as a keypad or touch display, may be used by an user to directly input into the server 10 information relating to a particular task to be performed in relation to one or more of the automated devices 20A, 20B, 20C.

Figure 4:
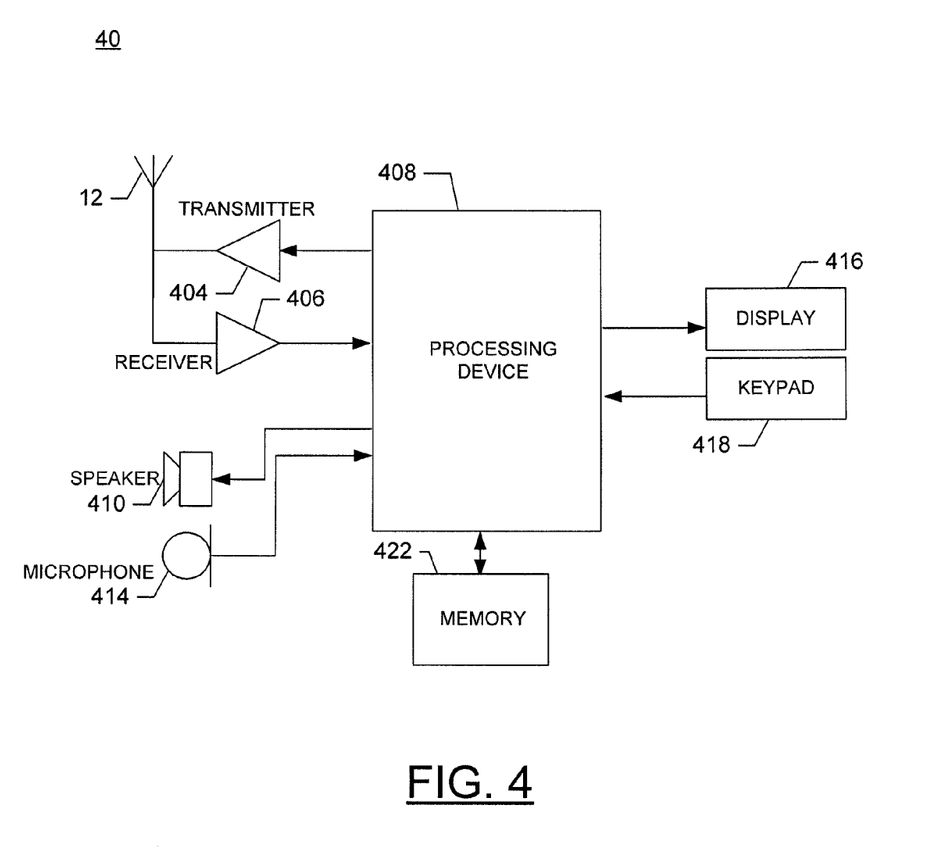
FIG. 4 is a schematic block diagram of a mobile device capable of operating in accordance with an exemplary embodiment of the present invention.

Reference is now made to FIG. 4, which illustrates one type of electronic device that could operate as the mobile device 40 described above in relation to FIG. 1. It should be understood, however, that the mobile device illustrated and hereinafter described is merely illustrative of one type of electronic device that would benefit from the present invention and, therefore, should not be taken to limit the scope of the present invention. In this regard, other types of mobile devices, such as personal digital assistants (PDAs), laptop computers, as well as other types of electronic systems including both mobile, wireless devices and fixed, wireline devices, can readily employ embodiments of the present invention. In particular, according to one exemplary embodiment, the mobile device 40 may comprise a simple headset or processor-free device including only a speaker and a microphone capable of conveying audible prompts generated by the central pharmacy server and conveying audible commands received from the user to the server for processing. In this exemplary embodiment, all processing of information may take place on the server 10 or on processing devices (e.g., personal computers (PCs)) associated with respective semi-automatic devices.

The mobile device 40 of exemplary embodiments includes various means for performing one or more functions in accordance with exemplary embodiments of the present invention, including those more particularly shown and described herein. It should be understood, however, that one or more of the entities may include alternative means for performing one or more like functions, without departing from the spirit and scope of the exemplary embodiments of present invention. More particularly, for example, as shown in FIG. 4, in addition to an antenna 402, the mobile device 40 may include a transmitter 404, a receiver 406, and means, such as a processing device 408, e.g., a processor, controller or the like, that processes signals and provides signals to and receives signals from the transmitter 404 and receiver 406, respectively. As discussed above, signals received by the receiver 406 may include, for example, instructions regarding one or more tasks to be performed in relation to one or more semi-automatic devices. These instructions may be received, for example, from the server 10, or directly from one or more sources (e.g., a nurse's workstation). The transmitter 404 may, in turn, transmit signals to corresponding semi-automatic devices instructing the device to perform a particular task. According to exemplary embodiments, the signals provided to and received from the transmitter 404 and receiver 406, respectively, include signaling information in accordance with the air interface standard of the applicable cellular system and also user speech and/or user generated data. In this regard, the mobile device can be capable of operating with one or more air interface standards, communication protocols, modulation types, and access types.

It is understood that the processing device 408, such as a processor, controller or other computing device, includes the circuitry required for implementing the visual, audio, and logic functions of the mobile device and is capable of executing application programs for implementing the functionality discussed herein. For example, the processing device may be comprised of various means including a digital signal processor device, a microprocessor device, and various analog to digital converters, digital to analog converters, and other support circuits. The control and signal processing functions of the mobile device are allocated between these devices according to their respective capabilities. The processing device 408 may include the functionality to operate one or more software applications, which may be stored in memory. For example, the controller may be capable of operating voice recognition software for translating between signals provided to and received from the transmitter 404 and receiver 406, respectively, and audio prompts/commands provided to and received from the input and output devices (discussed below), respectively.

The mobile device may also comprise means such as a user interface including, for example, a conventional earphone or speaker 410 (e.g., capable of outputting a voice prompt associated with an instruction received for performing a task), a microphone 414 (e.g., capable of inputting a voice command associated with a task to be performed), a display 416, all of which are coupled to the controller 408. The user input interface, which allows the mobile device to receive data, can comprise any of a number of devices allowing the mobile device to receive data, such as a keypad 418, a touch display (not shown), a microphone 414, or other input device. In embodiments including a keypad, the keypad can include the conventional numeric (0-9) and related keys (#, *), and other keys used for operating the mobile device and may include a full set of alphanumeric keys or set of keys that may be activated to provide a full set of alphanumeric keys. Although not shown, the mobile device may include a battery, such as a vibrating battery pack, for powering the various circuits that are required to operate the mobile device.

The mobile device can also include means, such as memory 422 for storing any of a number of pieces or amount of information and data used by the mobile device to implement the functions of the mobile device. The memory 422 may store, for example, computer program code for an application and other computer programs. For example, as discussed above, in one embodiment of the present invention, the memory 422 may store computer program code for receiving one or more tasks to be performed in relation to one or more semi-automatic devices, dynamically prioritizing the list based on a set of rules, and outputting a voice prompt associated with a task to a user, based on the dynamic prioritization. In yet another exemplary embodiment, the memory 422 may store information associated with one or more tasks performed within a predetermined period time (e.g., presorting information associated with medications to be restocked) until such information can be downloaded, for example, to the server 10.

Method of Remotely and Interactively Controlling Semi-Automatic Devices

Figure 5A:
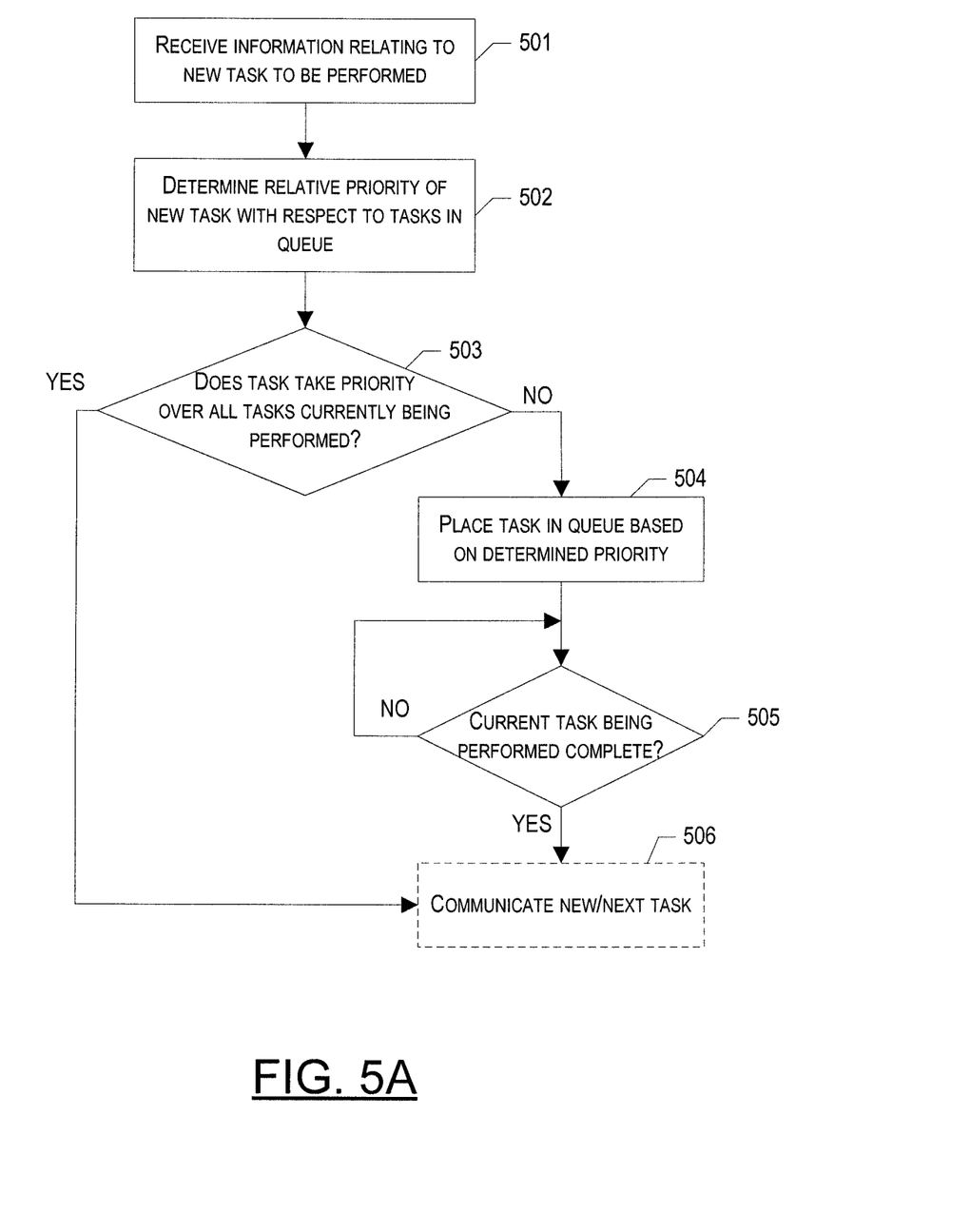
FIGS. 5A and 5B are flow charts illustrating the steps which may be taken in order to remotely and interactively control one or more semi-automatic devices in accordance with exemplary embodiments of the present invention.
Figure 5B:
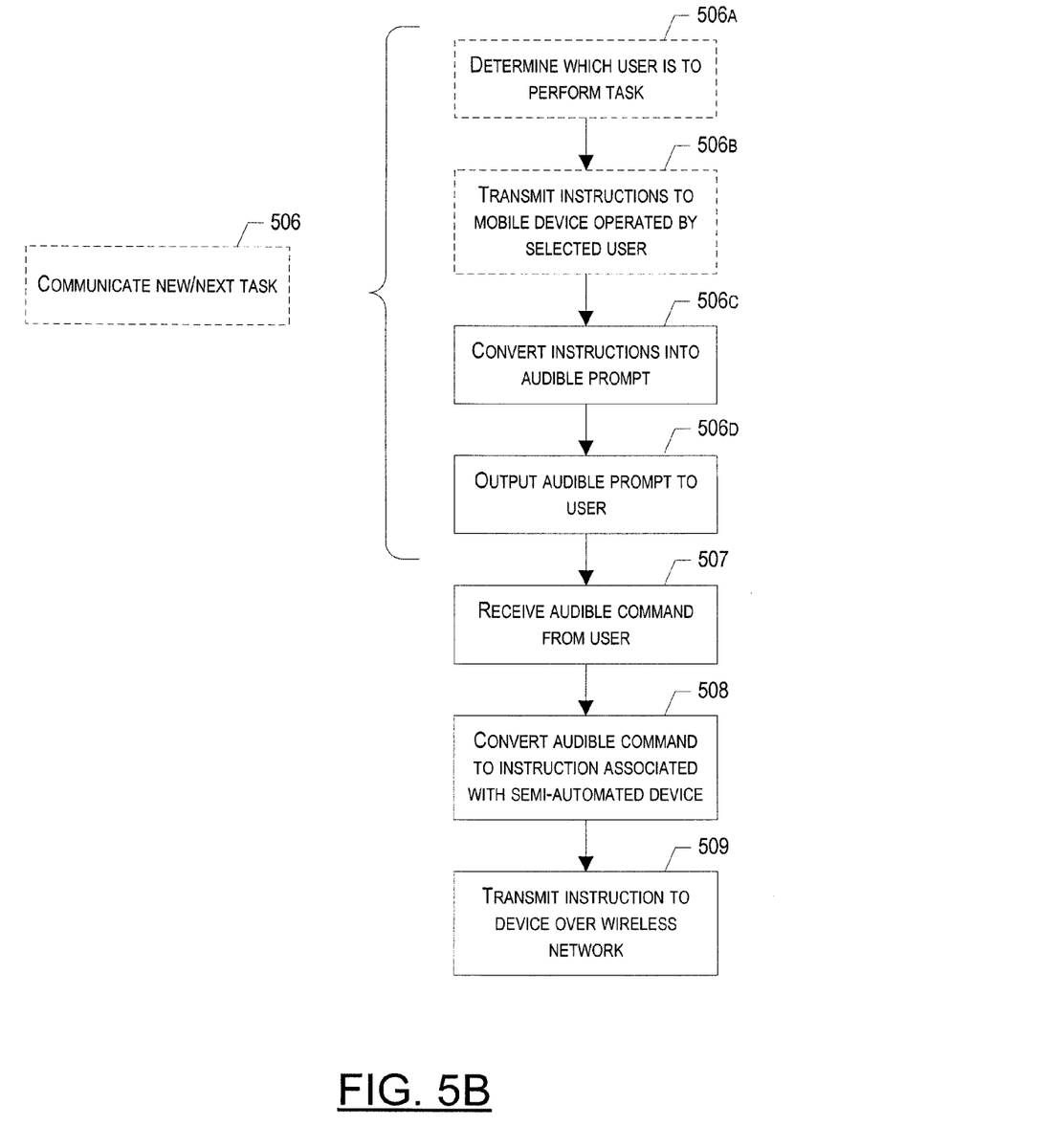

Reference is now made to FIGS. 5A and 5B, which illustrate the steps which may be taken in order to remotely and interactively control multiple semi-automatic devices in accordance with exemplary embodiments of the present invention. Beginning with FIG. 5A, as discussed above, while in one exemplary embodiment a server 10 (e.g., a central pharmacy server or main operating unit) may be responsible for receiving, storing and prioritizing the tasks to be performed in relation to one or more semi-automated devices, in another exemplary embodiment the mobile device 40 itself may have this responsibility. As a result, the steps shown in FIG. 5A may be performed by either the server 10 or the mobile device 40.

As shown, the process of one exemplary embodiment begins at Step 501 when information relating to a new task to be performed is received by the server 10 or mobile device 40. As noted above, the information may be received from a variety of different sources including, for example, an input device (e.g., keypad or touch display screen) associated with the server 10 or mobile device 40, and/or via a communication network from a remotely located device, such as a nurse's workstation. Upon receipt, the server 10 or mobile device 40 may determine, at Step 502, the relative priority of the new task with respect to any other tasks in the queue of tasks stored by the server 10 or mobile device 40. As noted above, this determination may be made based on a set of rules defining the relative priorities of the tasks based, for example, on the types of tasks to be performed, the device in relation to which the task is performed, and the like.

In Step 503 it is determined whether the task takes priority over at least one task currently being performed by a user operating a mobile device and working in association with the semi-automatic devices. If it is determined that the task does take priority over at least one task currently being performed, the new task is immediately communicated in Step 506. Alternatively, where the new task does not take priority over any currently performed task, the process continues to Step 504, where the new task is placed in the queue based on the relative priority determined in Step 502. The process then waits until a current task being performed is complete (Step 505), and then communicates the next task on the queue (Step 506).

While not shown, because circumstances may change over time that may affect the relative priorities of various tasks, if a predetermined amount of time passes while the process is waiting at Step 505 for a current task to be completed, the relative priorities of the various tasks in the queue may be automatically re-determined and updated.

Referring now to FIG. 5B, the previous step of communicating the new/next task (Step 406) may be performed differently depending upon the device responsible for storing and prioritizing the list of tasks. In particular, assuming, for example, that the server 10 queues and prioritizes the tasks, in this exemplary embodiment, communicating the new/next task may involve determining which user will perform the task (Step 506A) and transmitting an instruction to a mobile device operated by that user over a communication network (Step 506B). A determination of which user will perform the task may be based on any number of factors including, for example, the location of each user, the relative priority of the tasks currently being performed by each user, and/or the relative duration of tasks currently being performed and at what stage of the process the user is, just to name a few. Upon receipt of the instruction, the mobile device may convert the instruction into an audible prompt (Step 506C) and output the audible prompt to the user (Step 506D). Alternatively, where the mobile device is responsible for queuing and prioritizing the list of tasks, Steps 506A and 506B are unnecessary. The mobile device can simply convert the instruction into an audible prompt (Step 506C) and output the audible prompt to the user (Step 506D).

The process of exemplary embodiments then continues in a similar manner, regardless of whether the list is stored and prioritized by the server 10 or the mobile device 40. In particular, in Steps 507 through 509, respectively, the mobile device will receive an audible command from the user (in response to the audible prompt), convert the audible command into instructions associated with the corresponding semi-automated device, and wirelessly transmit the instruction to the device. In one exemplary embodiment, the audible command may be accompanied by some other input information (e.g., via a scanner or similar input device), which can be used in order to convert the command into an instruction. In one exemplary embodiment, converting the audible command into instructions may involve first converting the audible command into text using voice recognition software operating on the mobile device, and then determining which instruction corresponds with the converted text. The last step may, for example, involve comparing the text with a number of predefined instructions in order to select the corresponding instruction. Where none of the predefined instructions match up with the converted text, in one exemplary embodiment, the mobile device 40 may output an audible prompt requesting that the user repeat his or her audible command. In one exemplary embodiment, the audible prompts provided to the user may include choices from which the user may choose when responding to the audible prompt (e.g., "yes or no," "choice A, choice B or choice C," etc.), thus reducing the amount of interpretation required to determine the instruction associated with the user's audible command.

Exemplary Use Cases:

The following provides two practical examples of implementations of exemplary embodiments of the present invention. In the first scenario, a user may be standing in front of piece of semi-automated equipment, referred to as "Equip1," interacting physically with the device. The equipment may, for example, be McKesson's MedCarousel® medication storage and retrieval system and the user may, for example, be retrieving medications from the MedCarousel® system in order to fill one or more patient's bins with the medications needed for a given period of time (e.g., a day). At some point while the user is performing this task, the user may be audibly prompted by the mobile device he or she is operating that another piece of semi-automated equipment, referred to as "Equip2," across the room has a work request. Equip2 may, for example, be McKesson's ROBOT-Rx® medication storage and dispensing device, and the work request may, for example, be a request to dispense a first dose of medication for a particular patient. According to one exemplary embodiment, a first dose task may have priority, for example, over any task being performed by any other one of the devices; thus causing a central pharmacy server/main operating unit to push this instruction to the mobile device despite the fact that the user is in the process of completing a different task. In other words, upon receipt of the first dose task, the central pharmacy server/main operating unit may re-prioritize the queue of tasks to be performed by the various pieces of equipment, and then push the instruction to the mobile device based on this re-prioritization.

In response to the audible prompt, the user, via a voice command, may authorize the Equip2 to begin processing the work request, without having to physically walk over and interact with a computer, or other workstation associated with the piece of equipment. In particular, the mobile device may receive the user's voice command, translate the command into a text instruction, and wirelessly communicate the instruction to Equip2. Equip2 may then begin performing the task based on the authorization (e.g., the ROBOT-Rx® medication storage and dispensing device may begin filling the first dose request with an envelope delivery system). When Equip2 has completed the task, the user may be notified via an audible prompt from the mobile device, and the user can then, where necessary, walk over to perform any remaining physical actions associated with the task (e.g., the user may take the filled envelope, put it in a pneumatic tube, and send it to the appropriate destination).

The user may then be prompted by the central pharmacy server that a new task has been queued for another piece of semi-automated equipment, referred to as "Equip3." For example, McKesson's PACMED™ packager may need to package restock medications. The user, while walking back to Equip1 to resume activities there, may give a voice command to Equip3 to begin the operation (i.e., via the mobile device configured to translate the audible command into a text instruction and transmit the instruction wirelessly to the appropriate piece of equipment). While the user is operating at Equip 1, supplies necessary for Equip3 to complete its task may become depleted, thus requiring the user to intervene and resolve the problem at Equip3. In response, the user may receive a voice prompt from the mobile device that physical action is required with respect to Equip3. As above, a task requiring completion before a previously authorized task can be completed may, according to one exemplary embodiment, take priority over other tasks in the queue causing the central pharmacy server to place this task at the top of the queue and push the corresponding instruction to the mobile device immediately. In response to the voice prompt, the user may perform the necessary action, and then provide a voice command to the equipment, via the mobile device, that the action has been completed.

According to exemplary embodiments, the user, at anytime, may suspend any interruption in order to complete or concentrate on their current task, then revisit the system task queue when they are ready. The user may also, at anytime, visit one of the various computer workstations associated with any piece of equipment to interact more directly with the visual display and connected input devices to the equipment. The mobile device of exemplary embodiments of the present invention simply makes this physical interaction unnecessary to perform the tasks at hand.

An additional implementation of exemplary embodiments of the present invention arises where more than one mobile device is being simultaneously operated by several users in relation to one or more of the semi-automated devices. In this scenario, multiple users may be standing in front of piece of semi-automated equipment, referred to as "Equip1," (e.g., McKesson's IntelliShelf-Rx™ medication storage and dispensing device) interacting physically with the device. Each user may be audibly prompted to pick a different item that is visually indicated differently for each user. To illustrate, User1 may be told to pick Tablet A at the Green Light, User2 may be told to pick TabletB at the Red Light, User3 may be told to pick TabletA at the Blue Light. User1 might also be interrupted during such actions, to perform a higher priority task in accordance with the scenario described above.

CONCLUSION

As described above and as will be appreciated by one skilled in the art, embodiments of the present invention may be configured as a system, method or apparatus. Accordingly, embodiments of the present invention may be comprised of various means including entirely of hardware, entirely of software, or any combination of software and hardware. Furthermore, embodiments of the present invention may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Exemplary embodiments of the present invention have been described above with reference to block diagrams and flowchart illustrations of methods, apparatuses (i.e., systems) and computer program products. It will be understood that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus comprising:
a first input device configured to receive information associated with two or more tasks to be performed in relation to one or more medication storing, dispensing and packaging devices;
an output device configured to communicate an instruction, associated with at least one of the two or more tasks, to a user operating at least one of the one or more medication storing, dispensing and packaging devices;
a processor in communication with the first input device and the output device;
a memory in communication with the processor, said memory storing the information associated with the two or more tasks, said memory further storing an application executable by the processor, wherein the application is configured, upon execution, (a) to dynamically prioritize the two or more tasks based at least in part on a set of rules defining the relative priorities associated with the two or more tasks, (b) to prioritize one or more actions associated with at least one of the two or more tasks based at least in part on historical data representing options previously selected by one or more users in relation to the one or more actions, and (c) to automatically communicate, via the output device, an instruction, associated with one of the two or more tasks based at least in part on the dynamic prioritization, to a user operating at least one of the one or more medication storing, dispensing and packaging devices;
a second input device configured to receive an audible command from a user operating the apparatus in response to the instruction based at least in part on the dynamic prioritization, the application further configured, upon execution, to convert the audible command into an instruction associated with the at least one of the one or more medication storing, dispensing and packaging devices; and
a transmitter configured to wirelessly transmit the instruction converted from the audible command to the at least one of the one or more medication storing, dispensing and packaging devices for execution.

2. The apparatus of claim 1, wherein the set of rules defining the relative priorities of the two or more tasks comprises one or more rules defining a relative priority associated with respective ones of a plurality of types of tasks.

3. The apparatus of claim 2, wherein the set of rules defining the relative priorities of the two or more tasks further comprises one or more rules defining a relative priority associated with respective medication storing, dispensing and packaging devices.

4. The apparatus of claim 1, wherein an instruction associated with the at least one of the two or more tasks conveys the one or more actions in an order corresponding to the prioritization.

5. The apparatus of claim 4, the prioritization of the one or more actions associated with the at least one of the two or more tasks is further based at least in part on a probability that respective actions will be selected.

6. The apparatus of claim 5, wherein the application is further configured, upon execution, to determine the probability based at least in part on information of the historical data representing a frequency with which respective actions are selected.

7. The apparatus of claim 1, wherein the first input device comprises a receiver configured to receive the information over a network.

8. The apparatus of claim 1, wherein the first input device comprises a keyboard.

9. The apparatus of claim 1, wherein the output device comprises a transmitter, such that, in order to automatically communicate, via the output device, an instruction associated with one of the one or more tasks, the application is further configured to wirelessly transmit the instruction via the transmitter.

10. The apparatus of claim 9, wherein the application is further configured, upon execution, to determine to which of two or more mobile devices to transmit the instruction.

11. The apparatus of claim 1, wherein the output device comprises a speaker configured to output an audible prompt associated with the instruction, and wherein in order to automatically communicate, via the output device, an instruction associated with one of the one or more tasks, the application is further configured, upon execution, to convert the instruction into the audible prompt.

12. The apparatus of claim 1, wherein the second input device comprises a microphone.

13. A system comprising:
one or more medication storing, dispensing and packaging devices;
an apparatus configured to (a) receive and store information associated with two or more tasks to be performed in relation to the medication storing, dispensing and packaging devices, (b) dynamically prioritize the two or more tasks based at least in part on a set of rules defining the relative priorities associated with the two or more tasks, (c) prioritize one or more actions associated with at least one of the two or more tasks based at least in part on historical data representing options previously selected by one or more users in relation to the one or more actions, and (d) wirelessly communicate an instruction, associated with one of the two or more tasks based at least in part on the dynamic prioritization, to a mobile device of a user operating at least one of the one or more medication storing, dispensing and packaging devices;
the mobile device configured (a) to receive an audible command from the user in response to the instruction based at least in part on the dynamic prioritization, (b) to convert the audible command into an instruction associated with one of the medication storing, dispensing and packaging devices, and (c) to wirelessly transmit the instruction converted from the audible command to the at least one of the one or more medication storing, dispensing and packaging devices for execution.

14. The system of claim 13, wherein an instruction associated with the at least one of the two or more tasks conveys the one or more actions in an order corresponding to the prioritization.

15. The system of claim 14, wherein the prioritization of the one or more actions associated with the at least one of the two or more tasks is further based at least in part on a probability that respective actions will be selected.

16. The system of claim 15, wherein the apparatus is further configured to determine the probability based at least in part on information of the historical data representing a frequency with which respective actions are selected.

17. The system of claim 13, wherein the mobile device is further configured to convert the instruction into an audible prompt, and to output the audible prompt to a user operating the mobile device.

18. The system of claim 17, wherein the mobile device is further configured to receive an audible command from the user, to convert the audible command into an instruction, and to wirelessly transmit the instruction to a corresponding one of the medication storing, dispensing and packaging devices.

19. A method comprising:
receiving information associated with two or more tasks to be performed in relation to one or more medication storing, dispensing and packaging devices;
dynamically prioritizing the two or more tasks based at least in part on a set of rules defining the relative priorities associated with the two or more tasks;
prioritizing one or more actions associated with at least one of the two or more tasks based at least in part on historical data representing options previously selected by one or more users in relation to the one or more actions;
communicating an instruction, associated with one of the two or more tasks based at least in part on the dynamic prioritization, to a user operating at least one of the one or more medication storing, dispensing and packaging devices;
receiving an audible command from the user in response to the instruction based at least in part on the dynamic prioritization;
converting the audible command into an instruction associated with the at least one of the medication storing, dispensing and packaging devices; and
transmitting the instruction converted from the audible command to the at least one of the medication storing, dispensing and packaging devices for execution.

20. The method of claim 19, wherein dynamically prioritizing the two or more tasks comprises evaluating the relative priority associated with respective tasks and ordering the tasks based on the evaluation.

21. The method of claim 19, wherein an instruction associated with the at least one of the two or more tasks conveys the one or more actions in an order corresponding to the prioritization.

22. The method of claim 21, wherein the prioritization of the one or more actions associated with the at least one of the two or more tasks is further based at least in part on a probability that respective actions will be selected.

23. The method of claim 22 further comprising:
   determining the probability based at least in part on information of the historical data representing a frequency with which respective actions are selected.

24. The method of claim 19, wherein communicating an instruction associated with one of the two or more tasks comprises transmitting the instruction over a network.

25. The method of claim 19, wherein communicating an instruction associated with one of the two or more tasks comprises:
   converting the instruction into one or more audible prompts; and
   outputting the audible prompts.

26. An apparatus comprising:
   a first input device configured to receive an instruction associated with a task to be performed in relation to at least one of a set of medication storing, dispensing and packaging devices, wherein (a) the instruction is selected based on a dynamic prioritization of a plurality of tasks to be performed in relation to the at least one of the set of medication storing, dispensing and packaging devices, (b) the dynamic prioritization is based at least in part on a set of rules defining the relative priorities associated with the plurality of tasks, and (c) one or more actions associated with at least one of the plurality of tasks are prioritized based at least in part on historical data representing options previously selected by one or more users in relation to the one or more actions;
   an output device configured to output an audible prompt associated with the instruction;
   a processor in communication with the first input device and the output device;
   a memory in communication with the processor, said memory storing an application executable by the processor, wherein the application is configured, upon execution, to convert the instruction into the audible prompt for a user operating at least one of the one or more medication storing, dispensing and packaging devices;
   a second input device configured to receive an audible command in response to the instruction based on the dynamic prioritization, wherein the application is further configured, upon execution, to convert the audible command into an instruction associated with the at least one of the set of medication storing, dispensing and packaging devices; and
   a second output device configured to wirelessly transmit the instruction converted from the audible command to the at least one of the medication storing, dispensing and packaging devices for execution for execution.

27. The apparatus of claim 26, wherein the prioritization of the one or more actions associated with the at least one of the plurality tasks is further based at least in part on a probability that respective actions will be selected.

28. A computer program product for remotely and interactively controlling one more medication storing, dispensing and packaging devices, wherein the computer program product comprises at least one non-transitory computer-readable storage medium having computer-readable program code portions stored therein, the computer-readable program code portions comprising:
   a first executable portion for receiving information associated with two or more tasks to be performed in relation to one or more medication storing, dispensing and packaging devices;
   a second executable portion for (a) dynamically prioritizing the two or more tasks based at least in part on a set of rules defining the relative priorities associated with the two or more tasks and (b) prioritizing one or more actions associated with at least one of the two or more tasks based at least in part on historical data representing options previously selected by one or more users in relation to the one or more actions;
   a third executable portion for communicating an instruction, associated with one of the two or more tasks based at least in part on the dynamic prioritization, to a user operating at least one of the one or more medication storing, dispensing and packaging devices;
   a fourth executable portion for receiving an audible command in response to the instruction based at least in part on the dynamic prioritization;
   a fifth executable portion for converting the audible command into an instruction associated with one of the medication storing, dispensing and packaging devices; and
   a sixth executable portion for transmitting the instruction to the at least one of the medication storing, dispensing and packaging devices for execution.

29. The computer program product of claim 28, wherein the second executable portion is configured to evaluate the relative priority associated with respective tasks and order the tasks based on the evaluation.

30. The computer program product of claim 28, wherein the third executable portion is configured to transmit the instruction over a network.

31. The computer program product of claim 28, wherein the third executable portion is configured to:
   convert the instruction into one or more audible prompts; and
   output the audible prompts.

* * * * *